US011046628B2

(12) United States Patent
Ritter et al.

(10) Patent No.: US 11,046,628 B2
(45) Date of Patent: Jun. 29, 2021

(54) PROCESS FOR DEOXYFLUORINATION OF PHENOLS

(71) Applicants: STUDIENGESELLSCHAFT KOHLE MBH, Mülheim an der Ruhr (DE); PRESIDENT AND FELLOWS OF HARVARD COLLEGE, Cambridge, MA (US)

(72) Inventors: Tobias Ritter, Muelheim (DE); Constanze Neumann, Somerville, MA (US); Mohammad Hassan Beyzavi, Fayettevillle, AR (US); Martin Georg Strebl-Bantillo, Somerville, MA (US); Debashis Mandal, Fremont, CA (US)

(73) Assignee: STUDIENGESELLSCHAFT KOHLE MBH, Mülheim an der Ruhr (DE)

( * ) Notice: Subject to any disclaimer, the term of this patent is extended or adjusted under 35 U.S.C. 154(b) by 0 days.

(21) Appl. No.: 16/635,266

(22) PCT Filed: Jul. 10, 2018

(86) PCT No.: PCT/EP2018/068608
§ 371 (c)(1),
(2) Date: Jan. 30, 2020

(87) PCT Pub. No.: WO2019/025137
PCT Pub. Date: Feb. 7, 2019

(65) Prior Publication Data
US 2020/0369583 A1    Nov. 26, 2020

(30) Foreign Application Priority Data

Jul. 31, 2017    (EP) .................................... 17184127

(51) Int. Cl.
| | | |
|---|---|---|
| *C07C 17/16* | (2006.01) | |
| *C07B 59/00* | (2006.01) | |
| *C07C 231/12* | (2006.01) | |
| *C07D 451/02* | (2006.01) | |
| C07C 233/12 | (2006.01) | |
| C07F 15/00 | (2006.01) | |

(52) U.S. Cl.
CPC .............. *C07C 17/16* (2013.01); *C07B 59/00* (2013.01); *C07C 231/12* (2013.01); *C07D 451/02* (2013.01); C07B 2200/05 (2013.01); C07C 233/12 (2013.01); C07F 15/0046 (2013.01)

(58) Field of Classification Search
CPC ..... C07C 17/16; C07C 231/12; C07C 233/12; C07B 59/00; C07B 2200/05; C07D 451/02; C07F 15/0046
See application file for complete search history.

(56) References Cited

U.S. PATENT DOCUMENTS

| | | | | |
|---|---|---|---|---|
| 9,150,516 B2* | 10/2015 | Ritter | ................ | C07C 45/63 |
| 9,895,454 B2* | 2/2018 | Sergeev | ............... | C07H 19/052 |
| 2011/0054175 A1* | 3/2011 | Ritter | ................... | C07D 209/08 |
| | | | | 546/4 |
| 2011/0312903 A1* | 12/2011 | Ritter | ................ | C07C 45/63 |
| | | | | 514/26 |
| 2012/0095217 A1* | 4/2012 | Ritter | ................... | C07D 313/12 |
| | | | | 540/551 |
| 2012/0316341 A1* | 12/2012 | Ritter | ................ | C07C 17/16 |
| | | | | 546/48 |
| 2015/0252067 A1* | 9/2015 | Ritter | ................ | C07J 1/0059 |
| | | | | 560/30 |
| 2016/0251382 A1* | 9/2016 | Furstner | ............. | C07F 15/0046 |
| | | | | 548/402 |
| 2016/0272593 A1* | 9/2016 | Ritter | ................... | C07D 233/70 |

FOREIGN PATENT DOCUMENTS

| | | |
|---|---|---|
| WO | 2012/142162 A2 | 10/2012 |
| WO | 2015/058047 A2 | 4/2015 |

OTHER PUBLICATIONS

M. Strebl, Dissertation entitled "Impacting Neuroscience With Chemistry: HDAC Neuroimaging Enabled by [18F]-Fluorination Methodology", Harvard Library (Jun. 2017) (Year: 2017).*
M. Beyzavi et al., 3 ACS Central Science, 944-948 (2017) (Year: 2017).*
J. Rickmeieretal., 57 Angew. Chem. Int. Ed., 14207-14211 (2018) (Year: 2018).*
M. Strebl et al., 3 ACS Central Science, 1006-1014 (2017) (Year: 2017).*
P. Tang et al., 133 Journal of the American Chemical Society, 11482-11484 (2011) (Year: 2011).*
Konovalov et al., "Ruthenium-catalyzed nucleophilic fluorination of halobenzenes"; Chem Comm., 2015, 51, pp. 13527-13530.

* cited by examiner

*Primary Examiner* — Alexander R Pagano
(74) *Attorney, Agent, or Firm* — Norris McLaughlin, P.A.

(57) ABSTRACT

The present invention refers to a process for transition-metal-assisted $^{18}$F-deoxyfluorination of phenols. The transformation benefits from readily available phenols as starting materials, tolerance of moisture and ambient atmosphere, large substrate scope, and translatability to generate doses appropriate for positron emission tomography (PET) imaging.

13 Claims, 4 Drawing Sheets

PROCESS FOR DEOXYFLUORINATION OF PHENOLS

This application is a 371 of PCT/EP2018/068608, filed Jul. 10, 2018, which claims foreign priority benefit under 35 U.S.C. § 119 of the European Patent Application No. 17184127.3, filed Jul. 31, 2017, the disclosures of which are incorporated herein by reference.

The present invention refers to a process for transition-metal-assisted $^{18}$F-deoxyfluorination of phenols (aryl and heteroaryl compounds bearing a hydroxyl group). The transformation benefits from readily available phenols as starting materials, tolerance of moisture and ambient atmosphere, large substrate scope, and translatability to generate doses appropriate for positron emission tomography (PET) imaging.

Fluorination reactions with $^{18}$F in drug-like molecules enable the study of drug disposition and biochemical interactions in humans using positron emission tomography (PET). As PET-active nucleus, $^{18}$F is attractive for radiotracer design due to the prevalence of aryl fluorides in pharmaceuticals, the metabolic stability of the C—F bond, and the appropriate half-life (109.8 min) for small molecules when compared to other PET isotopes.

Although several modern late-stage $^{18}$F-fluorination methods have successfully expanded PET radiotracer synthesis, general methods, especially with large substrate scope and functional group tolerance are still scarce:

Here the inventors found the first $^{18}$F-deoxyfluorination reaction of phenols activated through $\eta^6$ $\pi$-coordination to a ruthenium complex. The method combines deoxyfluorination through a PhenoFluor-like mechanism, which ensures large functional-group-tolerance, with $\pi$ activation by ruthenium, which expands the substrate scope to even the most electron-rich phenols.

As a consequence, the new $^{18}$F-fluorination reaction has the potential to afford electron-rich aryl fluorides previously inaccessible through traditional $S_NAr$ reactivity, without some of the intrinsic limitations to other transition-metal mediated fluorination reactions. The inventors further found out that the transformation can serve to provide labelled materials suitable for PET imaging (FIG. 1).

Traditional nucleophilic aromatic substitution ($S_NAr$) reactions, including those with $^{18}$F-fluoride as nucleophile, require arene substrates with strong electron-withdrawing substituents. More modern $S_NAr$ reactions based on diaryl iodonium salts, or related reagents, enabled access to a wider range of fluoroarenes, including electron-rich arenes, but the synthesis of the diaryliodonium substrates can be challenging, especially for complex molecules. The inventors reported high-valent Pd- and Ni-based $^{18}$F-fluorination reactions, in which electrophilic $^{18}$F-reagents were generated in situ from $^{18}$F-fluoride.

Over the past five years, the field of late-stage fluorination has made several fundamental advances, yet, the development of general, reliable, scalable, and translatable $^{18}$F fluorination methods to achieve a measurable impact on clinical PET imaging is still outstanding. The data the inventors report here suggest that Ru-mediated deoxyfluorination may develop into such a method.

Cognizant of the challenges the inventors have observed with high-valent metal redox chemistry in $^{18}$F-fluorination, the inventors previously developed a metal-free $^{18}$F-deoxyfluorination of phenols (WO2015058047). The method is exceptionally functional group tolerant, to the best of the inventors' knowledge, more so than any other late-stage fluorination reaction. The functional group tolerance could be rationalized through a mechanism analysis: The key tetrahedral intermediate features a non-basic, neutral organofluoride (B), which rearranges to product (FIG. 2a below). The tetrahedral intermediate (B) is in equilibrium with its corresponding uronium fluoride ion pair (A). The equilibrium is inconsequential for reactions with excess $^{19}$F-fluoride. But because $^{18}$F-fluoride is used as the limiting reagent, detrimental side reactions from the ion pair (A) sequester $^{18}$F-fluoride irreversibly, especially if the equilibrium constant $K_1$ is small, as is expected for electron-rich phenols. As a consequence, although highly functional group tolerant, the substrate scope for current $^{18}$F-deoxyfluorination is limited; and electron-rich phenols cannot be $^{18}$F-deoxyfluorinated, despite the productive reaction with $^{19}$F.

The inventors' strategy to devise a more general reaction is targeted to increase the equilibrium constant K, specifically $K_2 \gg K_1$. In the present invention, the inventors disclose the successful implementation of a practical, robust ruthenium-mediated $^{18}$F-deoxyfluorination of both electron-rich and electron-poor phenols. The reaction retains the desirable features of deoxyfluorination without ruthenium and can tolerate nucleophilic functional groups such as amines.

In contrast to the redox active $^{18}$F-fluorination reactions with Pd, Ni, and Cu, the Ru center does not undergo redox chemistry, nor does the reaction proceed through high-valent complexes that could engage in undesired side reactions with amines or other nucleophilic groups.

Thus, the present invention is directed to a process for deoxyfluorination of an aromatic or heteroaromatic hydrocarbon bearing a hydroxyl group, named as phenol or phenolic compound in the scope of the invention, wherein in a first step, a Ru phenol complex is obtained through reaction of a Ru complex with said aromatic or heteroaromatic hydrocarbon bearing a hydroxyl group (phenol), and, in a second step, the obtained Ru phenol complex reacts with an uronium or imidazolium halogenide, preferably a chloride, in an organic solvent, in which the complexes are soluble, and the obtained solution is brought in contact with a fluoride source and then thermally treated whereby the fluorinated target compound is obtained. The process for forming the Ru-phenol-imidazolium-complex and the contacting step with the fluoride source may also be a one-pot-reaction.

The inventive process is exemplarily, not limiting to the compounds as shown, illustrated as follows:

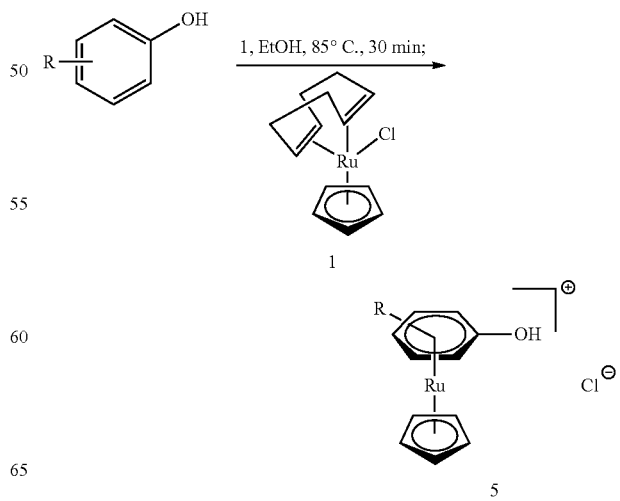

-continued

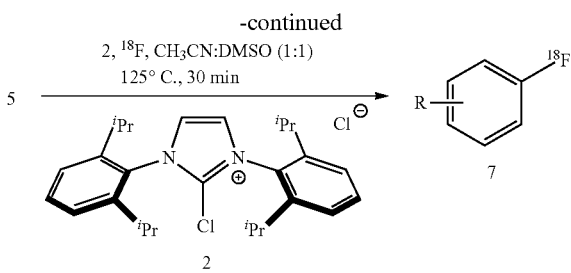

Generally, the Ru complex 1 contains an optionally substituted Cp-ligand and further any ligand which allows being replaced by the phenolic compound in the first step of the formation of the complex of Ru with the phenolic compound. Thus, the Ru complex 1 may be a complex, besides having an optionally substituted cyclopentadiene, with any of the ligands being selected from electron-donating ligands/substituents such as hydrogen, halogen, $CH_3CN$, cycloalkyldiene having 6 to 12 carbon atoms, such as COD, halogenide, cyanide and other electron donating substituents.

The Ru-complex 5 may be a cationic complex with an anionic counter ion X that is weakly coordinating, such as halogenide, $PF_6^-$, $SbF_6^-$, $BF_4^-$, $ClO_4^-$, $F_3CCOO^-$, $Tf_2N^-$, (Tf=trifluoromethanesulfonyl), $TfO^-$, tosyl, but the Ru-complex 5 can also be a neutral complex, if, for example, a proton is split off the hydroxyl group on the aromatic or heteroaromatic group.

The phenolic compound may be a C5 to C30, preferably C5 to C20 aromatic or heteroaromatic mono- to polycyclic ring system having at least one aromatic ring and one hydroxyl group on said aromatic ring, said ring system optionally being further substituted with straight chain, branched or cyclic alkyl, alkenyl or alkenyl having 1 to 20 carbon atoms, or heteroatoms being selected from halogen, N, O or S, each being optionally further substituted or each being optionally part of a aliphatic or aromatic ring system.

The solvent used in the inventive process is not decisive and may be selected by the skilled man, in consideration of the reaction partners, from aliphatic, cycloaliphatic solvents, alcohols, esters, ethers, ketones or mixtures thereof which may be substituted by one or more heteroatoms, such as hexane, $CHCl_3$, $CH_2Cl_2$, $CH_3CN$, ethyl acetate, acetone, THF, diethyl ether, DMSO or methyl tert-butyl ether or mixtures thereof, as long as it is not detrimental to the reaction.

Thus, as the key intermediate compound in the inventive process, an intermediate compound of the general formula (IV) is formed:

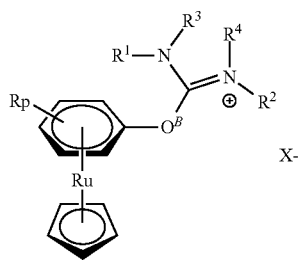 (IV)

which is also subject matter of the present invention and which can be converted to a Cp-Ru-(aromatic or heteroaromatic mono- to polycyclic ring)F complex by treatment with a fluorine source.

The inventions thus also comprises a process for converting a complex of the general formula (IV) into a Cp-Ru-(aromatic or heteroaromatic mono- to polycyclic ring)F complex by treatment with a fluorine source. As a further process step, the Cp-Ru-(aromatic or heteroaromatic mono- to polycyclic ring)F complex can be decomplexed according to standard procedures whereby the fluorinated aromatic or heteroaromatic mono- to polycyclic ring is obtained.

In said formula (IV),

represents a C5 to C30, preferably C5 to C20 aromatic or heteroaromatic mono- to polycyclic ring system having at least one aromatic or heteroaromatic ring and one oxygen $O^B$ bound on said aromatic or heteroaromatic ring, said ring system optionally being further substituted with at least one substituent $R_p$ selected from straight chain, branched or cyclic alkyl, alkenyl, alkynyl, aryl, heteroaliphatic or heteroaryl each having 1 to 20 carbon atoms, each being optionally further substituted by one or more heteroatoms, or a heteroatom, $R^1$ and $R^2$ are independently selected from the group consisting of C1 to C30, preferably C1-20 aliphatic, aromatic, heteroaliphatic or heteroaromatic hydrocarbons, each of which is optionally substituted with at least one substituent selected from C1-20 straight chain, branched or cyclic alkyl, alkenyl, alkynyl, aryl, heteroaryl or heteroatoms, each being optionally further substituted by one or more heteroatoms, $R^3$ and $R^4$ are independently selected from the group consisting of C1-30, preferably C1-20 aliphatic, aromatic, heteroaliphatic or heteroaromatic hydrocarbons, each of which is optionally substituted with at least one substituent selected from C1-20 straight chain, branched or cyclic alkyl, alkenyl, alkynyl, aryl, heteroaryl or heteroatoms, each being optionally further substituted by one or more heteroatoms, or $R^3$ and $R^4$ form a C4-20 hydrocarbon ring which may be saturated or unsaturated aliphatic, aromatic, heteoaliphatic or heteroaromatic, which is optionally substituted with at least one substituent selected from C1-20 straight chain, branched or cyclic alkyl, alkenyl, alkynyl, aryl, heteroaryl or heteroatoms, each being optionally further substituted by one or more heteroatoms, and X being an anion.

The inventive process can be carried out in a temperature range from elevated temperatures of 50° C. to 150° C. and it may proceed at ambient pressure up to elevated pressure, preferably at autogenous pressure, preferably in a closed container. If needed, the reaction can be carried out under a protective atmosphere such as argon.

Thus, the present invention is generally directed to a method of replacing a hydroxyl group on an aryl or heteroaryl compound, designated as phenol or phenolic compound in the context of the invention, with a fluorine atom, the method comprising reacting/contacting a compound of Formula (I):

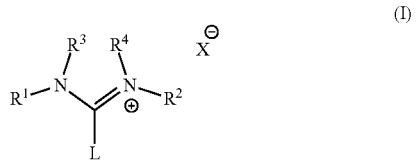

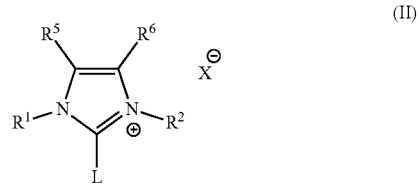

with a Cp-Ru-(aryl or heteroaryl)-complex (also designated as Cp-Ru-phenol complex) in the presence of a fluorine source under conditions sufficient to fluorinate the phenol compound, thereby providing a fluorinated (aryl or heteroaryl) compound, wherein, in Formula (I):

$R^1$ and $R^2$ are independently selected from the group consisting of C1-30, preferably C1-20 aliphatic, aromatic, heteroaliphatic or heteroaromatic hydrocarbons, each of which is optionally substituted with at least one substituent selected from C1-20 straight chain, branched or cyclic alkyl, alkenyl, alkynyl, aryl, heteroaryl, each being optionally further substituted by one or more heteroatoms, or heteroatoms, $R^3$ and $R^4$ are independently selected from the group consisting of C1-30, preferably C1-20 aliphatic, aromatic, heteroaliphatic or heteroaromatic hydrocarbons, each of which is optionally substituted with at least one substituent selected from C1-20 straight chain, branched or cyclic alkyl, alkenyl, alkynyl, aryl, heteroaryl, each being optionally further substituted by one or more heteroatoms, or heteroatoms, or $R^3$ and $R^4$ together form a C4-20 hydrocarbon ring which may be saturated or unsaturated aliphatic, aromatic, heteroaliphatic or heteroaromatic, each of which is optionally substituted with at least one substituent selected from C1-20 straight chain, branched or cyclic alkyl, alkenyl, alkynyl, aryl, heteroaryl, each being optionally further substituted by one or more heteroatoms, or heteroatoms, and X being an anion; and L being a leaving group, wherein the Ru phenol complex is a Ru complex with a C5 to C30, preferably C5 to C20 aromatic or heteroaromatic mono- to polycyclic ring system having at least one aromatic or heteroaromatic ring with one hydroxyl group on said ring, said ring system optionally being further substituted with straight chain, branched or cyclic alkyl, alkenyl or alkynyl having 1 to 20 carbon atoms, or heteroatoms being selected from halogen, N, O or S, each being optionally further substituted or each being optionally part of a aliphatic or aromatic ring system, and at least one further ligand preferably selected from cyclopentadienyl, optionally being further substituted by one or more heteroatoms being further substituted, preferably by C1-6 alkyl, halogen.

In the scope of the invention, heteroaryl bearing a hydroxy group might also be used for forming the Ru complex. In the above formula (I), $R^3$ and $R^4$ as well as $R^5$ and $R^6$ may be bound to each other via a single or double bond or via a hydrocarbon bridge including a single or double bond and may form the C4-20 hydrocarbon ring.

Furthermore, the invention comprises in some embodiments:

a method of replacing a hydroxyl group on an aryl or heteroaryl compound with a fluorine atom as defined before, wherein the compound (I) is represented by the following formula (II)

with a Ru phenol complex and a fluorine source under conditions sufficient to fluorinate the aryl or heteroaryl compound bearing the hydroxyl group, thereby providing a fluorinated aryl compound, wherein, in Formula (II):

$R^1$ and $R^2$ are independently selected from the group consisting of C1-6 alkyl, C6-10 aryl, C6-10 aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each being optionally further substituted by one or more heteroatoms;

$R^5$ and $R^6$ are independently selected from the group consisting of hydrogen, C1-6 alkyl, C2-6 alkenyl, C2-6 alkynyl, nitro, cyano, halo, C1-6 haloalkyl, C1-6 alkoxy, optionally substituted C6-10 aryl, optionally substituted C6-10 aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, each being optionally further substituted by one or more heteroatoms; or $R^5$ and $R^6$ may form together a C5-20 hydrocarbon ring which may be unsaturated or saturated aliphatic or aromatic including heteroatoms, optionally being substituted by hydrogen, C1-6 alkyl, C2-6 alkenyl, C2-6 alkynyl, nitro, cyano, halo, C1-6 haloalkyl, C1-6 alkoxy, optionally substituted C6-10 aryl, optionally substituted C6-10 aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, each being optionally further substituted by one or more heteroatoms;

X being an anion; and

L is a leaving group, wherein the Ru phenol complex is a Ru complex with an aryl or heteroaryl compound bearing a hydroxyl group (phenol) as a ligand and at least one further ligand preferably selected from cyclopentadienyl, optionally being substituted by C1-6 alkyl, haloalkyl or halogen.

a method of replacing a hydroxyl group on an aryl compound with a fluorine atom as defined before, wherein the compound of Formula (I) is represented by the following formula (III):

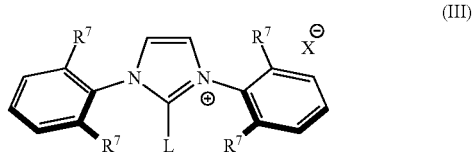

a method of replacing a hydroxyl group on an aryl compound with a fluorine atom as defined before, wherein L and/or X are selected from halide ions and carboxylate ions;

a method of replacing a hydroxyl group on an aryl compound with a fluorine atom as defined before wherein the fluorine source is a fluoride salt;

a method of replacing a hydroxyl group on an aryl compound with a fluorine atom as defined before wherein the fluorine source is a sodium, potassium, or cesium fluoride salt;

a method of replacing a hydroxyl group on an aryl compound with a fluorine atom as defined before wherein the fluoride source comprises $^{18}F$;

a method of replacing a hydroxyl group on an aryl compound with a fluorine atom as defined before wherein the fluoride source comprises $^{19}F$;

a method of replacing a hydroxyl group on an aryl compound with a fluorine atom as defined before wherein the Ru phenol complex is a Ru complex with one hydroxylaryl compound (phenol) as a ligand and one cyclopentadienyl ligand, optionally being substituted; and the use of a compound of Formula (I), (II) or (III) as defined above for deoxyfluorinating a Ru-phenol-complex in the presence of a fluorine source.

In the scope of the invention, heteroaryl bearing a hydroxy group might also be used for forming the Ru complex. In the above formulae (I) and (II), $R^3$ and $R^4$ as well as $R^5$ and $R^6$ may be bound to each other directly via a single or double bond or via a hydrocarbon bridge including a double bond and may form a hydrocarbon ring.

L is a leaving group and may have the same meaning as the anion X as $F^-$, $Cl^-$, $Br^-$, $J^-$, $NO_3^-$, $ClO_4^-$, $OH^-$, $H_2PO_4^-$, $HSO_4^-$, and a carboxylate ion (e.g., acetate, ethanoate, propanoate, benzoate, glycerate, lactate, tartrate, glycolate, imidazolide. Exemplary anions X include halide ions (e.g., $F^-$, $Cl^-$, $Br^-$, $J^-$, $NO_3^-$, $ClO_4^-$, $OH^-$, $H_2PO_4^-$, $HSO_4^-$, and carboxylate ions (e.g., acetate, ethanoate, propanoate, benzoate, glycerate, lactate, tartrate, glycolate, and the like) and are further defined below.

As used in the present specification, heteroatoms may be selected from halogen, N, O or S, each being optionally further substituted or each being optionally part of a aliphatic or aromatic ring system.

In some embodiments, the imidazolium compound is a compound of the formula (II) wherein, in Formula (I):

$R^1$ and $R^2$ are independently selected from the group consisting of C6-10 aryl, C6-10 aralkyl, 5-10 membered heteroaryl, 5-10 membered heteroaralkyl, each of which is optionally substituted at least one substituent selected from the group consisting of halogen, C1-6 alkyl, C2-6 alkenyl, C2-6 alkynyl, C1-6 haloalkyl, C1-6 alkoxy, optionally substituted with at least one heterosubstituent;

$R^5$ and $R^6$ are independently selected from the group consisting of hydrogen, C1-6 alkyl, C2-6 alkenyl, C2-6 alkynyl, C1-6 haloalkyl, C1-6 alkoxy, optionally substituted C6-10 aryl, optionally substituted C6-10 aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, optionally substituted with at least one heterosubstituent, L is a leaving group which is not detrimentally interacting in the process; and X represents an anion.

In some embodiments, the imidazolium compound is a compound of the formula (III) as represented as follows:

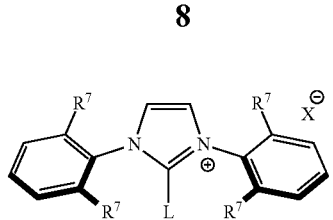

Wherein each $R^7$ is independently selected from halogen, optionally substituted C1-8 alkyl, C1-8 haloalkyl, C1-8 alkoxy, optionally substituted C6-12 aryl, and optionally substituted 6-12 membered heteroaryl, and wherein "substituted" refers to substituted with a substituent selected from the group consisting of alkyl (e.g., C1, C2, C3, C4, C5, C6, C7, C8, C9, C10, C11, C12 straight or branched chain alkyl), cycloalkyl, haloalkyl (e.g., perfluoroalkyl such as CF3), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as OCF3), halo, hydroxy, carboxy, carboxylate, cyano, nitro, amino, alkylamino, dialkylamino, phosphate, methylenedioxy (—O—CH$_2$—O— wherein oxygens are attached to vicinal atoms), ethylenedioxy, oxo, thioxo (e.g., C=S), imino (alkyl, aryl, aralkyl), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof), L is a leaving group which is not detrimentally interacting in the process; and X represents an anion.

In some embodiments, the imidazolium compound is a compound of the formula (III) as represented as follows:

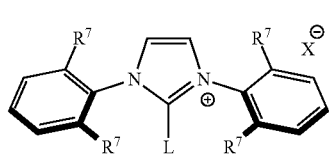

wherein $R^7$ represents iso-propyl, L is a leaving group which is not detrimentally interacting in the process; and X represents an anion.

The present invention is also directed to the use of a Ru complex and a imidazolium halogenide and a fluoride source for deoxyfluorination of a phenolic compound.

The methods described herein generally involve a fluorine source. The terms "fluorine source" and "fluoride source" are used interchangably herein. In certain embodiments, the fluorine source is a nucleophilic fluorine source (e.g., a fluoride, F). In certain embodiments, the fluorine source is commercially available. In certain embodiments, the fluorine source is also an inorganic fluorine source. Exemplary fluorine sources include sodium fluoride (NaF), cesium fluoride (CsF), potassium fluoride (KF), ammonium fluoride (NH4F), calcium fluoride (CaF2), lithium fluoride (LiF), aluminum fluoride (AlF3), barium fluoride (BaF2), silver fluoride (AgF and AgF2), tetramethylammonium fluoride (Me4NF), magnesium fluoride (MgF2), zinc fluoride (ZnF2), copper fluoride (CuF and CuF2), TBAF CBu4NF), cerium fluoride (CeF3), tin fluoride (SnF2), scandium fluoride (ScF3), and indium fluoride (InF3).

The fluorine source may be enriched with a particular isotope of fluorine. In certain embodiments, the fluorine source is labeled with 19F. In certain embodiments, use of a 19F-labeled fluorine source in the inventive method provides a fluorinated 19F-labeled organic compound.

In certain embodiments, the fluorine source is labeled with 18F (i.e., provides a 18F fluorine to the reaction mixture). In certain embodiments, use of a 18F-labeled fluorine source in the inventive method provides a fluorinated 18F-labeled organic compound such as a 18F-fluorinated aryl compound.

However, in certain embodiments, the fluorine source is labeled with a mixture of 18F and 19F. In certain embodiments, use of a mixture of 19F and 18F fluorine sources in the inventive method provides a mixture of fluorinated 19F-labeled organic compound and fluorinated 18F-labeled organic compound.

Definitions

Definitions of specific functional groups and chemical terms are described in more detail below.

When a range of values is listed, it is intended to encompass each value and subrange within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and acyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (acyclic, substituted, unsubstituted, branched or unbranched) having 1-6 carbon atoms.

As used herein, "alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, and one or more carbon-carbon double bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, and one or more carbon-carbon triple bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_5$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a nonaromatic cyclic hydrocarbon group having from 3 to 10 ring carbon atoms ("$C_{3-10}$ carbocyclyl") and zero heteroatoms in the nonaromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_5$), cyclononenyl ($C_5$), cyclodecyl ($C_{10}$), cyclodecenyl ($C_{10}$), octahydro-1H-indenyl ($C_5$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-8}$ cycloalkyl"). In some embodiments, a cycloalkyl group has 5 to 6 ring carbon atoms ("$C_{3-8}$ cycloalkyl"). In some embodiments, a cycloalkyl group has 5 to 10 ring carbon atoms ("$C_{3-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, sulfur, boron, phosphorus, and silicon ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, unsubstituted (an "unsubstituted heterocyclyl") or substituted (a "substituted heterocyclyl") with one or more substituents. In certain embodiments, the heterocyclyl group is unsubstituted 3-14 membered heterocyclyl. In certain embodiments, the heterocyclyl group is substituted 3-14 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-14 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix-ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. For purposes of this invention, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N (R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O) R$^{aa}$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc-}$;

each instance of R$^{aa}$ is, independently, selected from C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two Rec groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O) R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ haloalkyl, $C_{2-6}$ alkenyl, $C_{2-6}$ alkynyl, $C_{3-10}$ carbocyclyl, C6-10 aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2(C_{1-6}$ alkyl$)^+$ $X^-$, —$NH_3^+X^-$, —$N(OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$CO_2(C_{1-6}$ alkyl), —OC(=O)($C_{1-6}$ alkyl), —$OCO_2(C_{1-6}$ alkyl), —C(=O)$NH_2$, —C(=O)N($C_{1-6}$ alkyl$)_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl$)_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)N($C_{1-6}$ alkyl$)_2$, —C(=NH)NH($C_{1-6}$ alkyl), —C(=NH)$NH_2$, —OC(=NH)N($C_{1-6}$ alkyl$)_2$, —OC(NH)NH($C_{1-6}$ alkyl), —OC(NH)$NH_2$, —NHC(NH)N($C_{1-6}$ alkyl$)_2$, —NHC(=NH)$NH_2$, —$NHSO_2$($C_{1-6}$ alkyl), —$SO_2N(C_{1-6}$ alkyl$)_2$, —$SO_2NH$($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl$)_3$, —OSi($C_{1-6}$ alkyl$)_3$ —C(=S)N($C_{1-6}$ alkyl$)_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is an anionic counterion.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —$CO_2R^{aa}$, —C(=O)N($R^{bb}$)$_2$, —C(=$NR^{bb}$)$R^{aa}$, —C(=$NR^{bb}$)$OR^{aa}$, —C(=$NR^{bb}$)N($R^{bb}$)$_2$, C(=O)$NR^{bb}SO_2R^{aa}$, —C(=S)N($R^{bb}$)$_2$, —C(=O)$SR^{aa}$, or —C(=S)$SR^{aa}$, wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —$OR^{aa}$, —N($R^{cc}$)$_2$, —CN, —C(=O)$R^{aa}$, —C(=O)N($R^{bb}$)$_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)N($R^{cc}$)$_2$, —$SO_2N(R^{cc})_2$, —$SO_2R^{bb}$, —$SO_2OR^{bb}$, —$SOR^{aa}$, —C(=S)N($R^{cc}$)$_2$, —C(=O)$SR^{bb}$, —C(=S)$SR^{bb}$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —$OR^{aa}$, —N($R^{cc}$)$_2$, —C(=O)$R^{aa}$, —C(=O)N($R^{cc}$)$_2$, —$CO_2R^{aa}$, —$SO_2R^{aa}$, —C(=$NR^{cc}$)$R^{aa}$, —C(=$NR^{cc}$)$OR^{aa}$, —C(=$NR^{cc}$)N($R^{cc}$)$_2$, —$SO_2N(R^{cc})_2$, —$SO_2R^{cc}$, —$SO_2OR^{cc}$, —$SOR^{aa}$, —C(=S)N($R^{cc}$)$_2$, —C(=O)$SR^{cc}$, —C(=S)$SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

For example, nitrogen protecting groups such as amide groups (e.g., C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., C(=O)$OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyhel) carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, Nacetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyhethoxy]methylamine (SEM), N-3-acetoxpropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, and —Si(R$^{aa}$)$_3$, wherein R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1, 3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, $—R^{aa}$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc}_2$, $—P(R^{cc})_3$, $—P(=O)_2R^{aa}$, $—P(=O)(R^{aa})_2$, $—P(=O)(OR^{cc})_2$, $—P(=O)_2N(R^{bb})_2$, and $—P(=O)(NR^{bb})_2$, wherein $R^{aa}$, $R^{bb}$, and $R^{bb}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The invention is not intended to be limited in any manner by the above exemplary listing of substituents.

The term "complex" or "coordination complex" refers to an association of at least one atom such as Ru here or ion (which is referred to as a "central atom," "central ion," or "acceptor," and is usually a metallic cation) and a surrounding array of bound ligands or donors). Ligands are generally bound to a central atom or central ion by a coordinate covalent bond (e.g., ligands may donate electrons from a lone electron pair into an empty orbital of the central atom or central ion) and are referred to as being "coordinated" to the central atom or central ion. There are also organic ligands such as alkenes whose π-bonds can coordinate to empty orbitals of an acceptor. A complex may include one or more donors, which can be the same or different. A complex may also include one or more acceptors, which can be the same or different.

The term "ligand" refers to an ion or molecule that binds to a central atom or ion (e.g., a central metal atom or ion) to form a coordination complex. Ligands are usually electron donors, and the central atom or ion is electron acceptors. The bonding between the central atom or ion and the ligand typically involves formal donation of one or more of the ligand's electron pairs. The nature of such bonding can range from covalent to ionic, and the bond order can range from one to three. One central atom or ion may bind to one or more ligands of the same or different type. A ligand may be capable of binding a central atom or ion through multiple sites, usually because the ligand includes lone pairs on more than one atom of the ligand. Ligands in a complex may affect the reactivity (e.g., ligand substitution rates and redox) of the central atom or ion. Exemplary ligands include charge-neutral ligands ("ligand molecules," e.g., $CH_3CN$, amides (e.g., N,N-dimethylformamide (DMF), N,N-dimethylacetamide (DMA), or N-methyl-2-pyrrolidone (NMP)), dimethyl sulfoxide (DMSO), amines (e.g., ammonia; ethylenediamine (en); pyridine (py); 2,2'-bipyridine (bipy); and 1,10-phenanthroline (phen)), phosphines (e.g., $PPh_3$), ethers (e.g., tetrahydrofuran (THF), 2-methly-tetrahydrofuran, tetrahydropyran, dioxane, diethyl ether, methyl t-butyl ether (MTBE), dimethoxyethane (DME), and diglyme), ketones (e.g., acetone and butanone), chlorohydrocarbons (e.g., dichloromethane (DCM), chloroform, carbon tetrachloride, and 1,2-dichloroethane (DCE)), esters (e.g., propylene carbonate and ethyl acetate), CO, $N_2$, water, and alkenes and cycloalkenes or cycloalkyldienes, and anionic ligands ("ligand ions," e.g., halides, hydride, alkyls, $S_2^-$, $S—CN^-$, $O—NO_2$, $N—N_2^-$, $O—H^-$, $[O—C(=O)—C(=O)—O]_2^-$, $O—N—O^-$, $N=C=S^-$, $CN^-$).

A "anionic counterion" or shortly "anion" is a negatively charged group associated with a positively charged group in order to maintain electronic neutrality. A anionic counterion may carry one or more (e.g., two, three, or four) negative charges. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, ptoluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, ethanoate, propanoate, benzoate, glycerate, lactate, tartrate, glycolate, and the like), $BF_4^-$, $PF_4^-$, $PF_6^-$, $SbF_6^-$, $B[3,5-(CF_3)_2C_6H_3]_4^-$, $BPh_4^-$, $Al(OC(CF_3)_3)_4^-$, and a carborane anion (e.g., $CB_{11}H_{12}^-$ or $(HCB_{11}Me_5Br_6)^-$).

The term "isotopes" refers to variants of a particular chemical element such that, while all isotopes of a given element share the same number of protons in each atom of the element, those isotopes differ in the number of neutrons. The term "radioactivity" or "radioactive decay" refers to the process by which a nucleus of an unstable isotope (e.g., $^{18}F$) loses energy by emitting particles or rays (e.g., alpha particles, beta particles, and gamma rays) of ionizing radiation. Such an unstable isotope or a material including the unstable isotope is referred to as "radioactive." The Curie (Ci) is a non-SI (non-International System of Units) unit of radioactivity and is defined as 1 Ci=$3.7 \times 10^{10}$ decays per second. The term "specific activity" refers to the unit radioactivity of a material (e.g., a compound of Formula (I), or a salt, tautomer, stereoisomer, or isotopically labeled derivative (e.g., $^{18}F$ labeled derivative) thereof). In certain embodiments, the term "specific activity" refers to the radioactivity of a material per micromole (μmol) of the material.

BRIEF DESCRIPTION OF THE DRAWINGS

The invention is further illustrated by the attached Figures.

Figure 3:
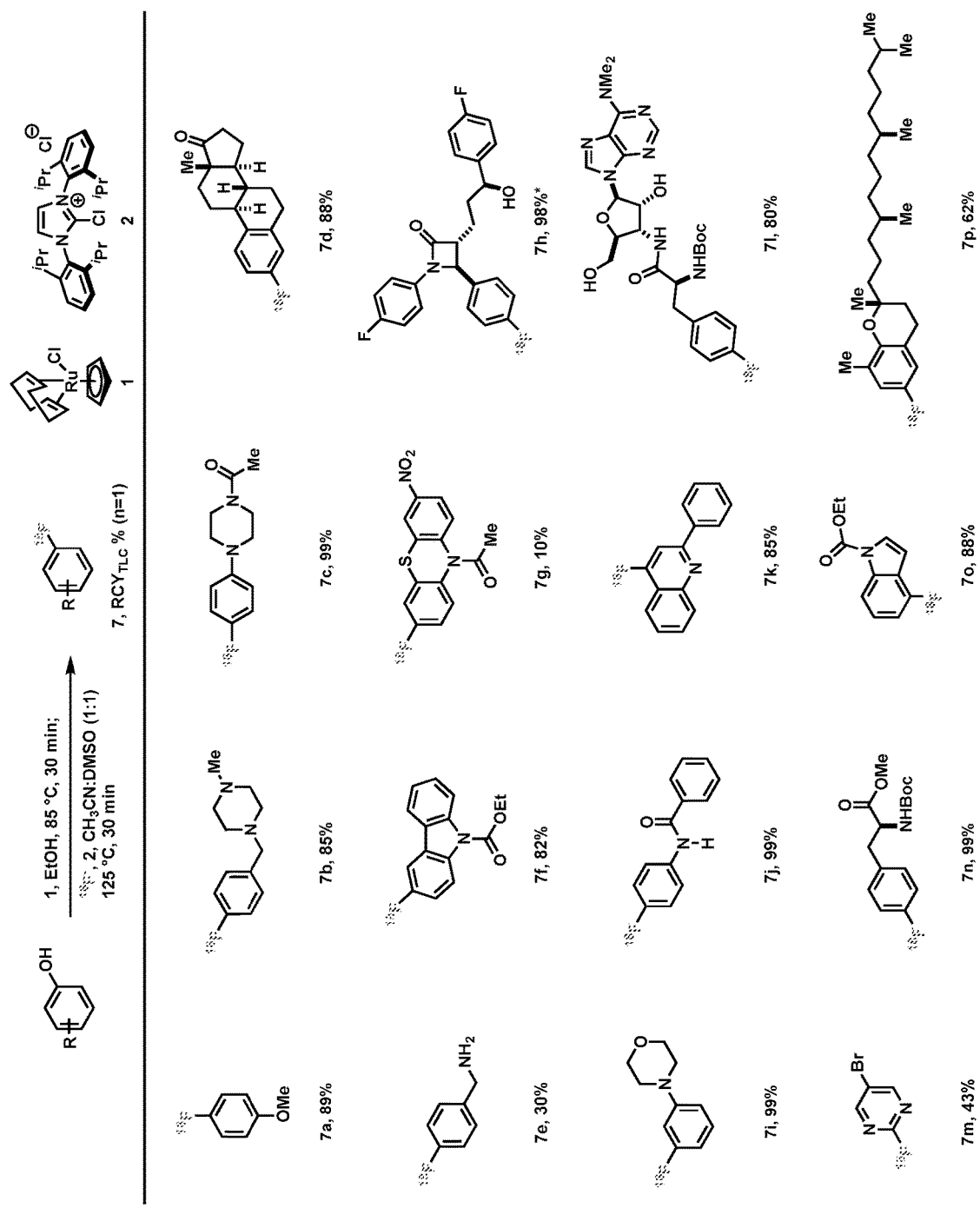
Figure 4:
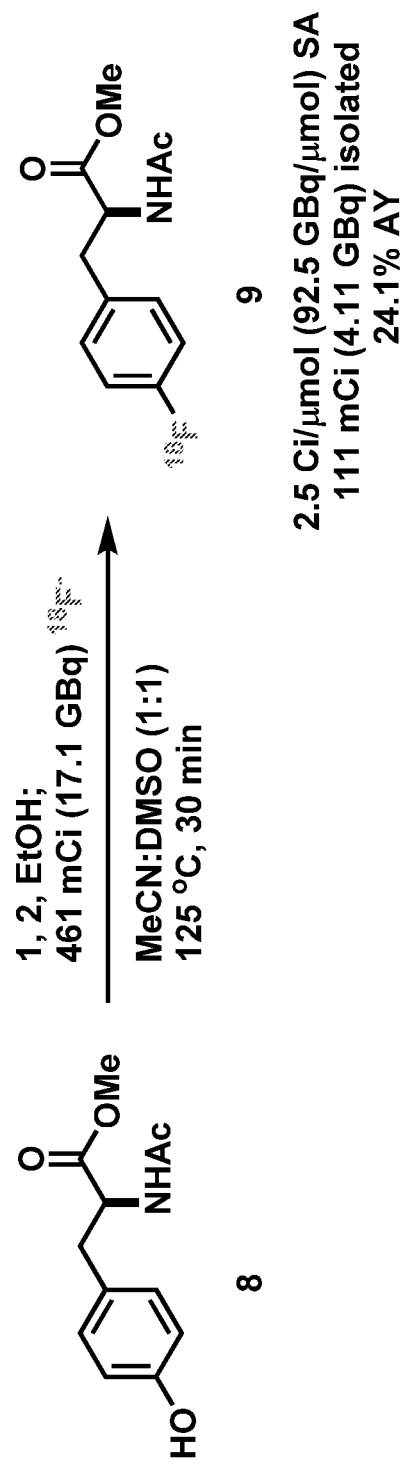

2a) Concerted nucleophilic aromatic substitution ($CS_NAr$) via B to furnish the fluorinated arene. $K_1$: equilibrium constant. Ar=2,6-diisopropylphenyl 2b) The ruthenium fragment decreases the electron density of the phenol, which renders the tetrahedral intermediate more favorable—$K_2>>K_1$. Isotopologue [$^{19}$F]6 was synthesized from 5 in 75% yield to confirm the identity of [$^{18}$F]6;

FIG. 3. Substrate table for ruthenium-mediated $^{18}$F-deoxyfluorination of phenols. $RCY_{TLC}$=Radiochemical yield determined as fraction of product radioactivity of total counts by radio-TLC; *26% activity yield;

FIG. 4. Fully automated ruthenium-mediated $^{18}$F-deoxyfluorination of tyrosine derivative. 111 mCi (4.11 GBq) activity yield AY (24.1%) is non-decay-corrected. As shown in FIG. 3, heating the air and moisture stable Ru complex CpRu(COD)Cl (1) with a phenol in ethanol for 30 min at 85° C. affords a solution of ruthenium phenol complex, e.g. 5, subsequent addition of chloroimidazolium chloride 2 provides a solution, which is used to elute $^{18}$F-fluoride off an anion exchange cartridge. After addition of a 1:1 DMSO/acetonitrile (v/v) solution, the reaction mixture is heated for 30 min to afford aryl fluorides. No precautions to exclude moisture or air are necessary at any point in the process.

As regards the experimental results, in line with the inventors' goal, electron-rich substrates like anisole (7a) and dialkylaniline derivatives (7c) show high radiochemical yields by TLC($RCY_{TLC}$). A variety of functional groups is tolerated, most importantly basic amines (7b, c, i, l) which can present a major limitation to several available radiofluorination methods. Protic functional groups (7e, j, n) are unproblematic and phenolic hydroxyl groups can be selectively deoxyfluorinated in the presence of unprotected aliphatic alcohols without affecting carbinol stereochemistry (7h, l). Additionally, several heterocyclic scaffolds, including pyrimidines (7m), indoles (7o) and quinolines (7k) are good substrates for the reaction. Ortho-substitution is tolerated (7k, o).

The overall yield of the reaction is affected by the RCY and elution efficiency (EE) of [$^{18}$F]fluoride off the anion exchange cartridge, and both were addressed when optimizing reaction conditions. Chloride as X-type ligand for CpRu(COD)X gave higher yields than other evaluated ligands. EE and RCY improved with higher concentration and molar excess of both 1 and 2. The minimal increases in yield obtained by more than three equivalents of 1 and 2 did not justify the expenditure of reagents and additional purification difficulties. Both EE and RCY were higher when ethanol was present in the reaction mixture. While more than 30% ethanol was detrimental to the fluorination, low solvent volumes were impractical to handle, and the inventors continued the inventors' work with 50 µL ethanol in 400 µL total reaction volume. Although several salt additives increased elution efficiency, the gain was offset by a reduction in RCY. None of the additives investigated improved the overall yield. Reaction temperatures below 125° C. and reaction times less than 30 min afforded lower yields of product.

For any $^{18}$F-radiolabeling methodology to be practically useful, it needs to be amenable to automation on commercial radiosynthesis modules. On an Elixys (Sofie Biosciences) radiosynthesizer, the inventors were able to perform the reaction in a fully automated fashion: From 461 mCi (17.1 GBq) of $^{18}$F-fluoride obtained in aqueous solution from a cyclotron, the inventors were able to isolate 111 mCi (4.11 GBq) of purified, protected $^{18}$F-fluorophenylalanine derivative 9 within 80 min (FIG. 4). Additional reformulation and filtration, as is required for human PET tracer synthesis, formally resulted in 82.3 mCi (3.05 GBq) of reformulated, purified 9 (see SI for detail). The stereochemical purity of the starting material was maintained throughout the reaction. Initially, yields of the automated syntheses were more than tenfold lower than in manual experiments. The main factors responsible for the lower yields were identified as vial size and the associated headspace, and the use of 4 mL instead of 10 mL reactors resolved the issue. It is crucial to ensure that an internal temperature of 125° C. is reached when using a vial adapter. In commercial radiosynthesis systems for which smaller vials are not commonly available, high pressure is an alternative strategy to counteract the larger headspace. For example, in a Siemens Explore FDG4 system, an increase in pressure from 30 kPa to 205 kPa during the reaction improved the RCY toward protected fluorophenylalanine fivefold (see SI for details).

Figure 1:
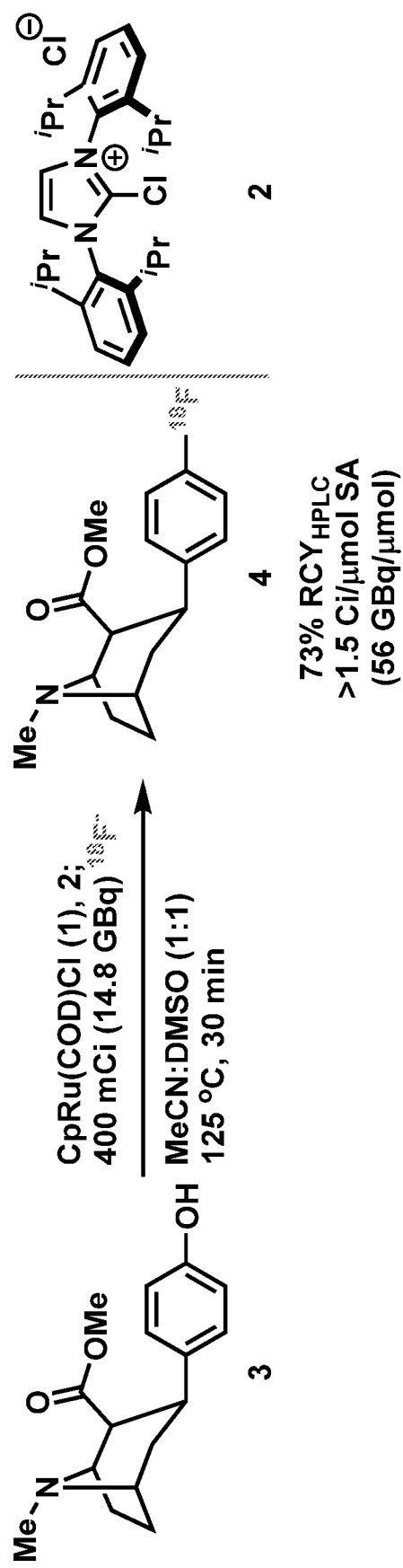
FIG. 1. Synthesis of β-CFT via ruthenium-mediated deoxyfluorination. $RCY_{HPLC}$=Radiochemical yield determined as fraction of product radioactivity of total counts by radio-HPLC.
Figures 2A, 2B:
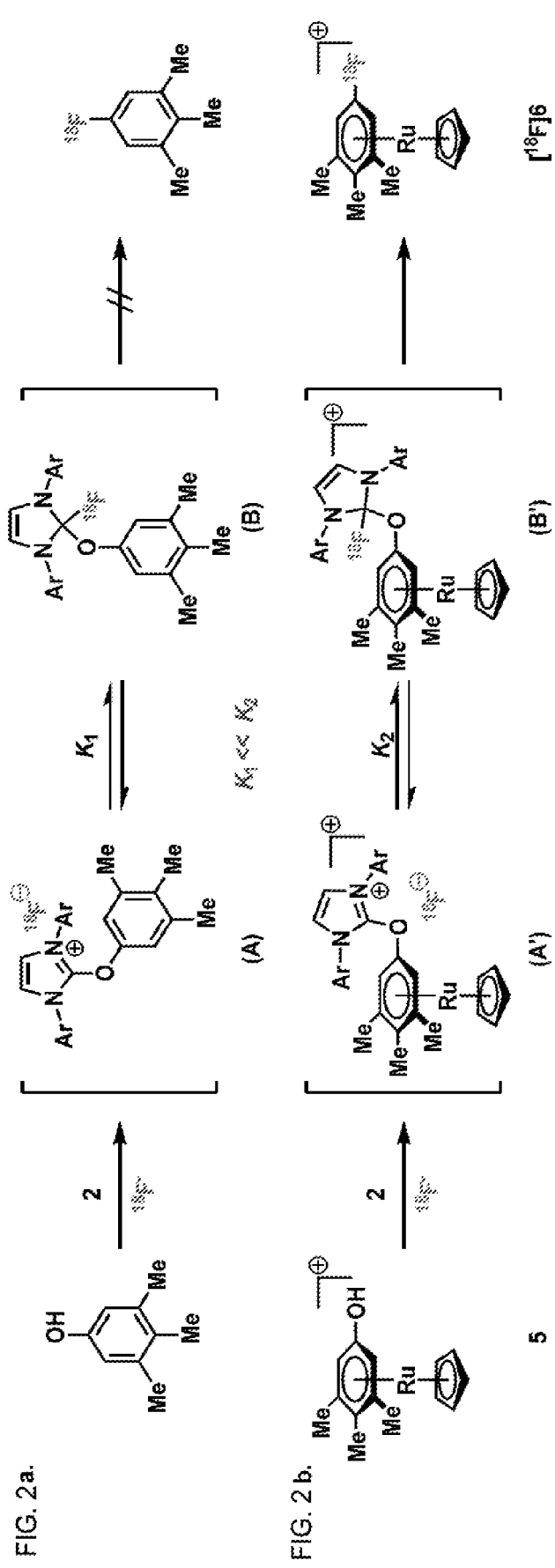
FIG. 2a and FIG. 2b.

The PhenoFluor reagent is known to facilitate a concerted nucleophilic aromatic substitution mechanism, which enables deoxyfluorination of electron-rich phenol substrates.[6] The inventors' computational results (see FIG. 1) suggest that coordination of the RuCp fragment withdraws sufficient electron density from the phenol substrate that a classic $S_NAr$ mechanism via a Meisenheimer complex (MHC) is preferred. DFT-calculated reaction barriers are 5.3 kcal·mol$^{-1}$ for fluoride attack ($TS_1$) and 7.0 kcal·mol$^{-1}$ for leaving group loss ($TS_2$). The inventors consider the barriers remarkably low for C—F bond formation, and, hence, the potential of η$^6$-coordination for radiofluorination of other arene electrophiles may be a promising research endeavor. Attempts to isolate reaction intermediates in the deoxyfluorination of phenols with $^{19}$F-fluoride only yielded the aryl fluoride product complexed to Ru (eg. 6), which corroborates the low deoxyfluorination barriers obtained computationally. Decomplexation of the aryl fluoride product from the Ru fragment requires elevated reaction temperatures, and, currently, is the rate-limiting step in the sequence. Because [$^{18}$F]fluoroarene dissociation is rate-limiting, the inventors note that [$^{18}$F]fluoroarene complexed to the RuCp fragment can be observed as byproduct if reaction times are too short.

The ruthenium-mediated dexoyfluorination presents a valuable addition to the radiochemical toolbox. Very electron rich substrates are challenging to fluorinate with conventional radiofluorination reactions, but unproblematic for this approach. Basic amines and ortho-substitution are fully compatible. The substrates are readily accessible and stable phenols. The reaction is operationally simple, can be executed in air in the presence of moisture, and automation is established. The method is broadly applicable and easy to adapt in a radiopharmaceutical production environment.

The invention is further illustrated by the following exemplary preparations.

Experimental Part

General Procedure for [$^{18}$F]Deoxyfluorination of Phenols

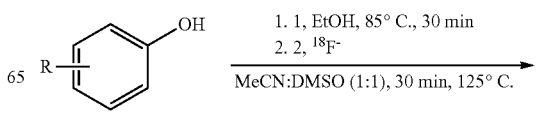

-continued

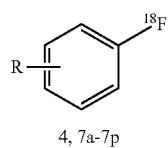

4, 7a-7p

A phenol (8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. for 30 min. The vial was removed from the heating block and allowed to stand for 3 min at 23° C. To the vial, imidazolium chloride 2 (12 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride (typically 50 uL) was loaded with a syringe onto a QMA anion exchange cartridge (Chromafix 30-PS—HCO$_3$) and the radioactivity of the trapped $^{18}$F-fluoride was measured (Table S1). The cartridge was washed with MeCN (1.0 mL). The cartridge was inverted and fitted with a female×female Luer adapter. With the syringe, which contained the corresponding solution of phenol-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (Table S1). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The products were characterized by comparing the radio-HPLC trace of the reaction mixtures with the HPLC UV traces of the authentic reference samples, respectively.

All $^{18}$F-labeled molecules were characterized by comparing the retention time of the product (γ-trace) to the retention time of an authentic reference sample. Note: radioactivity chromatographs are offset by 0.15 min on account of the delay introduced by the spatial separation between the diode array detector and the radioactivity detector.

TABLE S1

The amounts of initial radioactivity trapped, the amount eluted, and the RCYs of [$^{18}$F]deoxyfluorination of phenols, estimated by TLC.

| Entry | Product | Initial radioactivity (mCi, GBq) | Eluted radioavtivity (mCi, GBq) | Elution efficiency (%) | RCY (%) |
|---|---|---|---|---|---|
| 1 | 4 | 8.0, 0.30 | 5.1, 0.19 | 64 | 67 |
| 2 | 7a | 7.5, 0.28 | 4.9, 0.18 | 66 | 89 |
| 3 | 7b | 5.9, 0.22 | 4.4, 0.16 | 75 | 85 |
| 4 | 7c | 5.2, 0.19 | 3.3, 0.12 | 63 | 99 |
| 5 | 7d | 6.2, 0.23 | 4.6, 0.17 | 73 | 88 |
| 6 | 7e | 4.2, 0.16 | 3.0, 0.11 | 71 | 30 |
| 7 | 7f | 4.3, 0.16 | 2.7, 0.10 | 64 | 82 |
| 8 | 7g | 6.9, 0.26 | 4.0, 0.15 | 58 | 10 |
| 9 | 7h | 5.9, 0.22 | 3.9, 0.14 | 66 | 98 |
| 10 | 7i | 5.6, 0.21 | 3.1, 0.12 | 55 | 99 |
| 11 | 7j | 7.2, 0.27 | 4.8, 0.18 | 67 | 99 |
| 12 | 7k | 6.0, 0.22 | 4.6, 0.17 | 77 | 85 |
| 13 | 7l | 6.5, 0.24 | 3.5, 0.13 | 54 | 80 |
| 14 | 7m | 5.1, 0.20 | 3.5, 0.13 | 67 | 43 |
| 15 | 7n | 7.3, 0.27 | 4.6, 0.17 | 62 | 99 |

TABLE S1-continued

The amounts of initial radioactivity trapped, the amount eluted, and the RCYs of [$^{18}$F]deoxyfluorination of phenols, estimated by TLC.

| Entry | Product | Initial radioactivity (mCi, GBq) | Eluted radioavtivity (mCi, GBq) | Elution efficiency (%) | RCY (%) |
|---|---|---|---|---|---|
| 16 | 7o | 10.7, 0.40 | 6.8, 0.25 | 64 | 88 |
| 17 | 7p | 6.0, 0.22 | 3.0, 0.11 | 49 | 62 |

[$^{18}$F]-β-CFT (4)

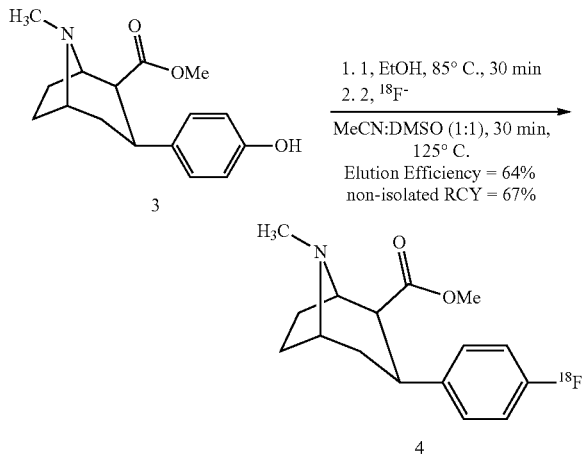

Phenol 3 (3.9 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (8.0 mCi, 0.30 GBq). The cartridge was washed with MeCN (1.0 mL). The cartridge was inverted and fitted with a female×female Luer adapter. With the syringe, which contained the corresponding solution of 3-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (5.1 mCi, 0.19 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product [$^{18}$F]-β-CFT (4) was characterized by comparing the radio-HPLC trace of the reaction mixture with the HPLC UV traces of the authentic reference sample. The authentic reference (β-CFT) (5 mg) was purchased from Sigma-Aldrich as β-CFT naphthalenedisulfonate monohydrate and then the naphthalenedisulfonate was removed from the sample using 5 coupled Sep-Pak Plus C18 Environmental Cartriges (WAT036800) from Waters connected in series. The sample was loaded onto the C18 cartridges, and a HPLC pump was used for elution with the following mobile phases: 0.1% formic acid in water (A), 0.1% formic acid in acetonitrile (B). Program: starting from 5% (B) to 95% (B) as a gradient over 12 min with flow rate 4.0 mL/min.

[$^{18}$F]1-(Fluoro)-4-methoxybenzene (7a)

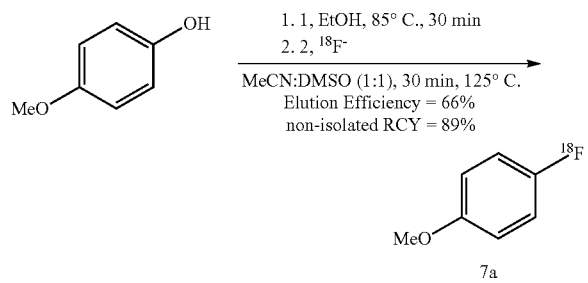

4-Methoxyphenol (1.1 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (7.5 mCi, 0.28 GBq). The cartridge was washed with MeCN (1.0 mL). The cartridge was inverted and fitted with a female×female Luer adapter. With the syringe, which contained the corresponding solution of 4-methoxyphenol-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (4.9 mCi, 0.18 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7a was characterized by comparing the radio-HPLC trace of the reaction mixture with the HPLC UV traces of the authentic reference sample.

[$^{18}$F]Benzylpiperazin 7b

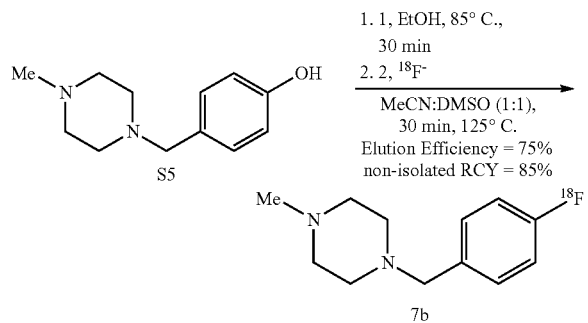

Phenol S5 (1.7 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (5.9 mCi, 0.22 GBq). The cartridge was washed with MeCN (1.0 mL). The cartridge was inverted and fitted with a female×female Luer adapter. With the syringe, which contained the corresponding solution of S5-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (4.4 mCi, 0.16 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7b was characterized by comparing the radio-HPLC trace of the reaction mixture with the HPLC UV traces of the authentic reference sample.

[$^{18}$F]Piperazin 7c

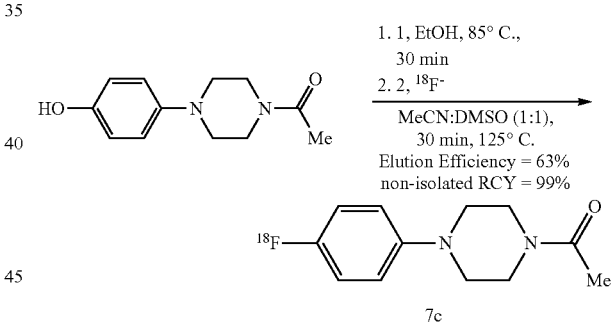

1-(4-(4-Hydroxyphenyl)piperazin-1-yl)ethan-1-one (1.9 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (5.2 mCi, 0.19 GBq). The cartridge was washed with MeCN (1.0 mL). The cartridge was inverted and fitted with a female×female Luer adapter. With the syringe, which contained the corresponding solution of 1-(4-(4-hydroxyphenyl)piperazin-1-yl)ethan- 1-one-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (3.3 mCi, 0.12 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7c was characterized by comparing the radio-HPLC trace of the reaction mixture with the HPLC UV traces of the authentic reference sample.

[$^{18}$F]Estrone 7d

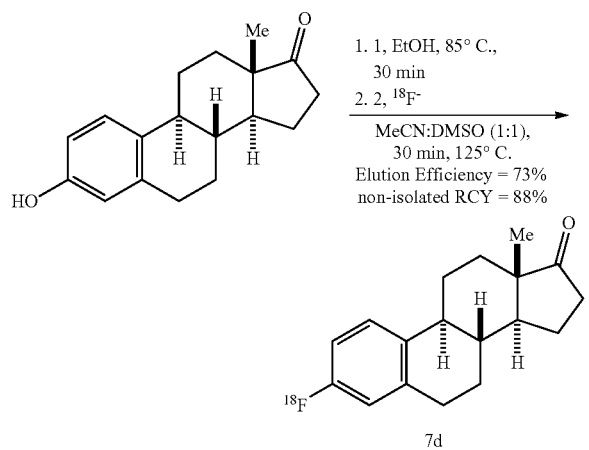

Estrone (2.3 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (6.2 mCi, 0.23 GBq). The cartridge was washed with MeCN (1.0 mL). The cartridge was inverted and fitted with a female×female Luer adapter. With the syringe, which contained the corresponding solution of estrone-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (4.6 mCi, 0.17 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7d was characterized by comparing the radio-HPLC trace of the reaction mixture with the HPLC UV traces of the authentic reference sample.

[$^{18}$F](4-(Fluoro)phenyl)methanamine (7e)

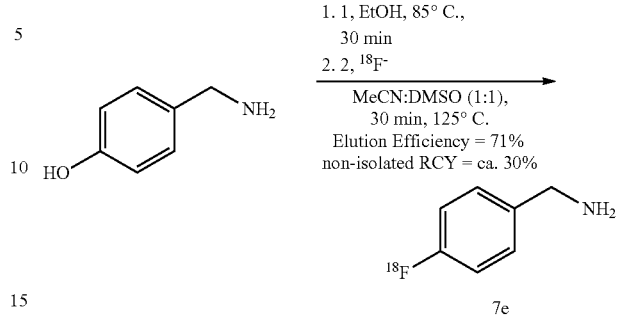

4-(Aminomethyl)phenol (1.1 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (4.2 mCi, 0.16 GBq). The cartridge was washed with MeCN (1.0 mL). The cartridge was inverted and fitted with a female×female Luer adapter. With the syringe, which contained the corresponding solution of 4-(aminomethyl)phenol-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (3.0 mCi, 0.11 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7e was characterized by comparing the radio-HPLC trace of the reaction mixture with the HPLC UV traces of the authentic reference sample.

Note: Lewis basic compounds, such as amines, can form unproductive ruthenium coordination compounds. These are typically visible by HPLC as broad peaks within the first minutes after the solvent front. We attribute the relatively low yield of 7e to the formation of such compounds and consequently suggest protection of primary amines, despite fundamental compatibility with the reaction.

[$^{18}$F]Ethyl 3-(fluoro)-9H-carbazole-9-carboxylate (7f)

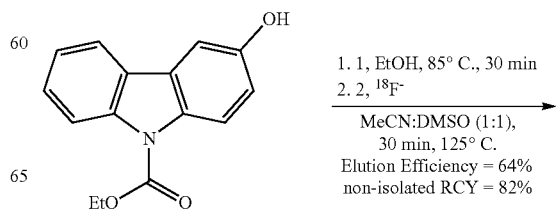

-continued

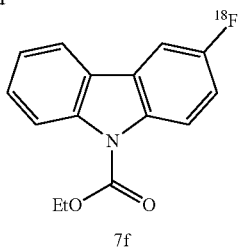

7f

Ethyl 3-hydroxy-9H-carbazole-9-carboxylate (2.2 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (4.3 mCi, 0.16 GBq). The cartridge was washed with MeCN (1.0 mL). The cartridge was inverted and fitted with a female×female Luer adapter. With the syringe, which contained the corresponding solution of ethyl 3-hydroxy-9H-carbazole-9-carboxylate-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (2.7 mCi, 0.10 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7f was characterized by comparing the radio-HPLC trace of the reaction mixture with the HPLC UV traces of the authentic reference sample.

[$^8$F]Phenothiazin 7q

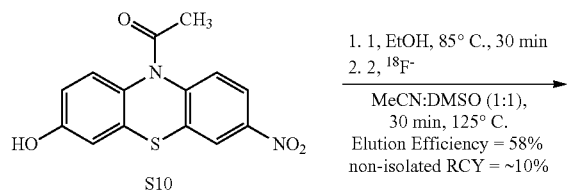

1. 1, EtOH, 85° C., 30 min
2. 2, $^{18}$F-

MeCN:DMSO (1:1),
30 min, 125° C.
Elution Efficiency = 58%
non-isolated RCY = ~10%

-continued

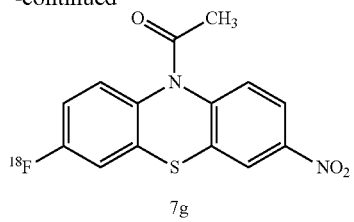

7g

Phenol S10 (2.6 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (6.9 mCi, 0.26 GBq). The cartridge was washed with MeCN (1.0 mL). The cartridge was inverted and fitted with a female×female Luer adapter. With the syringe, which contained the corresponding solution of S10-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (4.0 mCi, 0.15 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7g was characterized by comparing the radio-HPLC trace of the reaction mixture with the HPLC UV traces of the authentic reference sample.

[$^{18}$F]Fluorodeoxyezetimibe (7h)

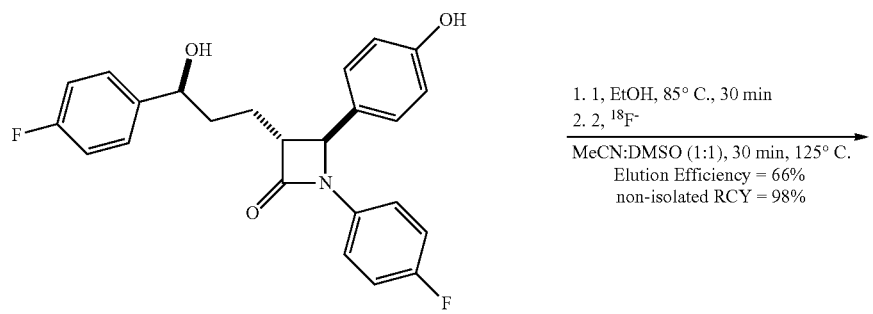

1. 1, EtOH, 85° C., 30 min
2. 2, $^{18}$F-

MeCN:DMSO (1:1), 30 min, 125° C.
Elution Efficiency = 66%
non-isolated RCY = 98%

S19

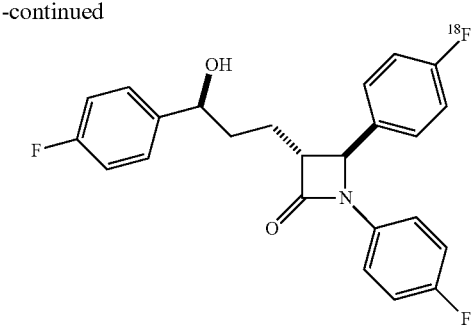

7h

Ezetimibe (S19) (3.5 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (5.9 mCi, 0.22 GBq). The cartridge was washed with MeCN (1.0 mL). The cartridge was inverted and fitted with a female×female Luer adapter. With the syringe, which contained the corresponding solution of S19-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (3.9 mCi, 0.14 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7h was characterized by comparing the radio-HPLC trace of the reaction mixture with the HPLC UV traces of the authentic reference sample.

[$^{18}$F](4-(3-(Fluoro)phenyl)morpholine) (7i)

3-Morpholinophenol (1.5 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (5.6 mCi, 0.21 GBq). The cartridge was washed with MeCN (1.0 mL). The cartridge was inverted and fitted with a female×female Luer adapter. With the syringe, which contained the corresponding solution of 3-morpholinophenol-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (3.1 mCi, 0.12 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7i was characterized by comparing the radio-HPLC trace of the reaction mixture with the HPLC UV traces of the authentic reference sample.

[$^{18}$F]4-Fluorobenzanilide (7j)

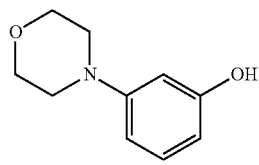

1. 1, EtOH, 85° C., 30 min
2. 2, [18]F-

MeCN:DMSO (1:1),
30 min, 125° C.
Elution Efficiency = 55%
non-isolated RCY = 99%

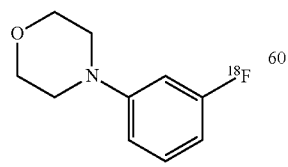

7i

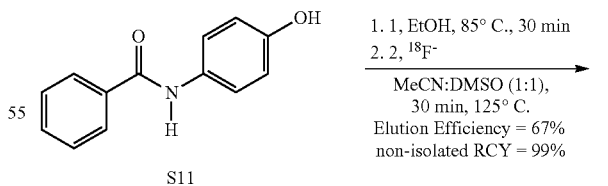

S11

1. 1, EtOH, 85° C., 30 min
2. 2, [18]F-

MeCN:DMSO (1:1),
30 min, 125° C.
Elution Efficiency = 67%
non-isolated RCY = 99%

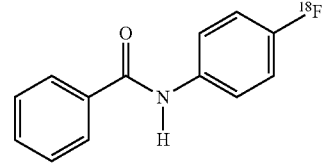

7j

N-(4-Hydroxyphenyl)benzamide (S11) (1.8 mg, 8.7 µmol, 1.0 eq.) and [CpRu(cod)Cl] (1) (8.0 mg, 26 µmol, 3.0 eq.) were added to EtOH (50 µL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 µmol, 3.0 eq.) and 150 µL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (7.2 mCi, 0.27 GBq). The cartridge was washed with MeCN (1.0 mL). The cartridge was inverted and fitted with a female×female Luer adapter. With the syringe, which contained the corresponding solution of S11-ruthenium complex and 2, the $^{18}$F-fluoride was eluted into a 1 dram (3.7 mL) borosilicate vial. The cartridge was washed with DMSO (150 µL), followed by DMSO: MeCN (50 µL, 1:1 (v/v)) and the radioactivity of the eluted solution was measured (4.8 mCi, 0.18 GBq). The reaction vial, which contained 400 µL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7j was characterized by comparing the radio-HPLC trace of the reaction mixture with the HPLC UV traces of the authentic reference sample.

[$^{18}$F]4-(Fluoro)-2-phenylquinoline (7k)

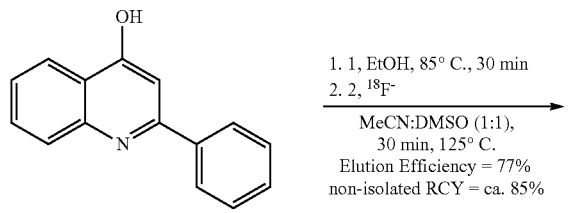

1. 1, EtOH, 85° C., 30 min
2. 2, $^{18}$F$^-$

MeCN:DMSO (1:1),
30 min, 125° C.
Elution Efficiency = 77%
non-isolated RCY = ca. 85%

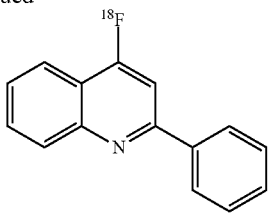

7k

2-Phenylquinolin-4-ol (1.9 mg, 8.7 µmol, 1.0 eq.) and [CpRu(cod)Cl] (1) (8.0 mg, 26 µmol, 3.0 eq.) were added to EtOH (50 µL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 µmol, 3.0 eq.) and 150 µL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (6.0 mCi, 0.22 GBq). The cartridge was washed with MeCN (1.0 mL). The cartridge was inverted and fitted with a female×female Luer adapter. With the syringe, which contained the corresponding solution of 2-phenylquinolin-4-ol-ruthenium complex and 2, the $^{18}$F-fluoride was eluted into a 1 dram (3.7 mL) borosilicate vial. The cartridge was washed with DMSO (150 µL), followed by DMSO: MeCN (50 µL, 1:1 (v/v)) and the radioactivity of the eluted solution was measured (4.6 mCi, 0.170 Bq). The reaction vial, which contained 400 µL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7k was characterized by comparing the radio-HPLC trace of the reaction mixture with the HPLC UV traces of the authentic reference sample.

[$^{18}$F]Purin 71

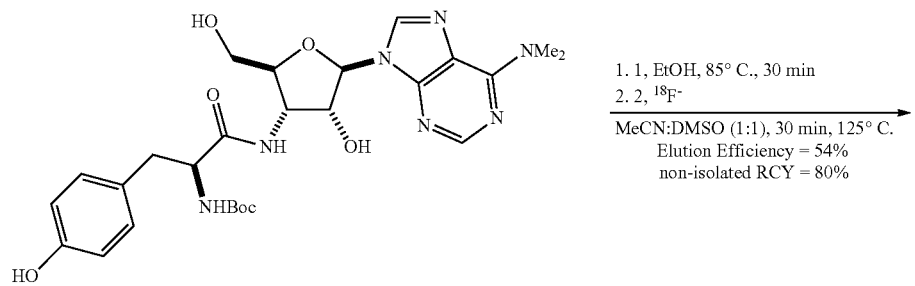

S13

1. 1, EtOH, 85° C., 30 min
2. 2, $^{18}$F$^-$

MeCN:DMSO (1:1), 30 min, 125° C.
Elution Efficiency = 54%
non-isolated RCY = 80%

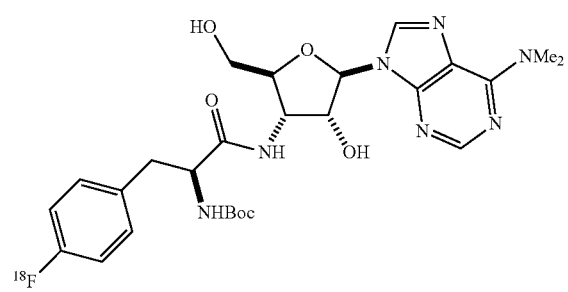

71

Purin S13 (3.9 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto QMA anion exchange cartridge (Chromafix 30-PS—HCO$_3$) and the radioactivity of the trapped $^{18}$F-fluoride was measured (6.5 mCi, 0.24 GBq). The cartridge was washed with MeCN (1.0 mL). The cartridge was inverted and fitted with a female×female Luer adapter. With the syringe, which contained the corresponding solution of S13-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (3.5 mCi, 0.13 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7l was characterized by comparing the radio-HPLC trace of the reaction mixture with the HPLC UV traces of the authentic reference sample.

[$^{18}$F]5-Bromo-2-(fluoro)pyrimidine (7m)

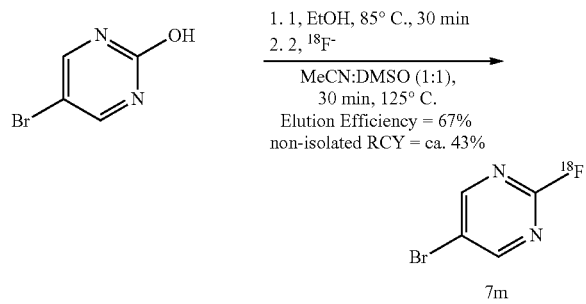

5-Bromopyrimidin-2-ol (1.5 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (5.1 mCi, 0.19 GBq). The cartridge was washed with MeCN (1.0 mL). The cartridge was inverted and fitted with a female×female Luer adapter. With the syringe, which contained the corresponding solution of 5-bromopyrimidin-2-ol-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (3.5 mCi, 0.13 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7m was characterized by comparing the radio-HPLC trace of the reaction mixture with the HPLC UV traces of the authentic reference sample.

Figure S45. UV-HPLC trace of 5-bromo-2-fluoropyrimidine as the reference.

[$^{18}$F]L-tyrosinate 7n

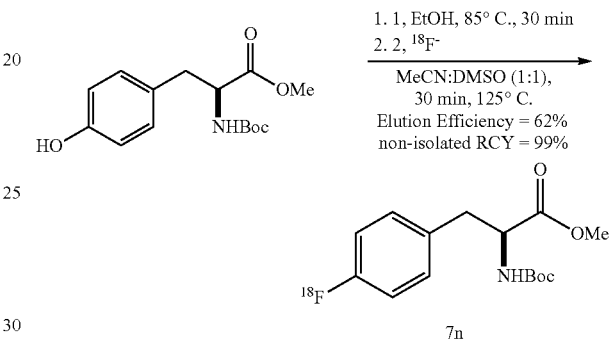

Methyl (tert-butoxycarbonyl)-L-tyrosinate (2.5 mg, 8.7 μmol, 1.0 eq.) and [CpRu(cod)Cl] (1) (8.0 mg, 26 μmol, 3.0 eq.) were added to EtOH (50 μL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 μmol, 3.0 eq.) and 150 μL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (7.3 mCi, 0.27 GBq). The cartridge was washed with MeCN (1.0 mL). The cartridge was inverted and fitted with a female×female Luer adapter. With the syringe, which contained the corresponding solution of methyl (tert-butoxycarbonyl-L-tyrosinate-ruthenium complex and 2, the $^{18}$F-fluoride was eluted into a 1 dram (3.7 mL) borosilicate vial. The cartridge was washed with DMSO (150 μL), followed by DMSO: MeCN (50 μL, 1:1 (v/v)) and the radioactivity of the eluted solution was measured (4.6 mCi, 0.17 GBq). The reaction vial, which contained 400 μL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7n was characterized by comparing the radio-HPLC trace of the reaction mixture with the HPLC UV traces of the authentic reference sample.

[$^{18}$F]Ethyl 4-(fluoro)-1H-indole-1-carboxylate (7o)

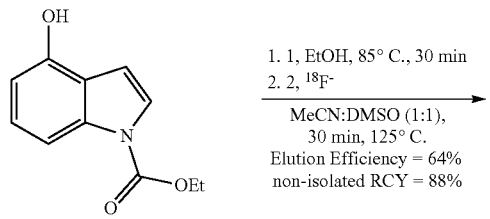

[$^{18}$F]Chromane 7p

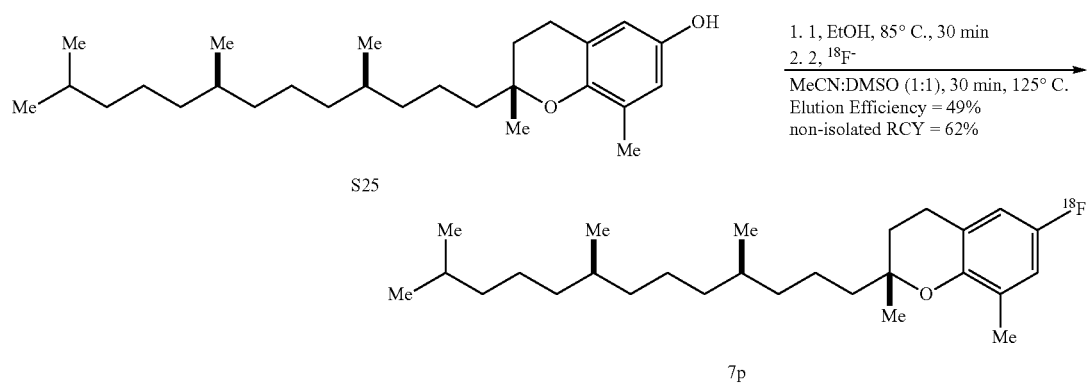

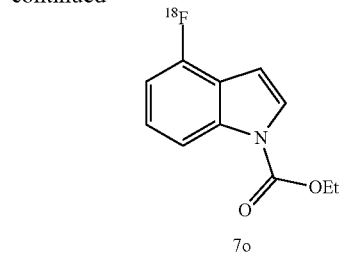

Ethyl 4-hydroxy-1H-indole-1-carboxylate (1.7 mg, 8.7 µmol, 1.0 eq.) and [CpRu(cod)Cl] (1) (8.0 mg, 26 µmol, 3.0 eq.) were added to EtOH (50 µL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 µmol, 3.0 eq.) and 150 µL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (10.7 mCi, 0.40 GBq). The cartridge was washed with MeCN (1.0 mL). The cartridge was inverted and fitted with a female×female Luer adapter. With the syringe, which contained the corresponding solution of ethyl 4-hydroxy-1H-indole-1-carboxylate-ruthenium complex and 2, the $^{18}$F-fluoride was eluted into a 1 dram (3.7 mL) borosilicate vial. The cartridge was washed with DMSO (150 µL), followed by DMSO: MeCN (50 µL, 1:1 (v/v)) and the radioactivity of the eluted solution was measured (6.8 mCi, 0.25 GBq). The reaction vial, which contained 400 µL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7o was characterized by comparing the radio-HPLC trace of the reaction mixture with the HPLC UV traces of the authentic reference sample.

[$^{18}$F]Chromane 7p (+)-δ-Tocopherol (S25) (3.4 mg, 8.7 µmol, 1.0 eq.) and [CpRu(cod)Cl] (1) (8.0 mg, 26 µmol, 3.0 eq.) were added to EtOH (50 µL, c=0.80 M) in a 0.5 dram (1.8 mL) borosilicate glass vial. The vial was capped, and the reaction mixture was stirred at 85° C. (heating block temperature) for 30 min. The vial was removed from the heating block and allowed to stand for 3 min at 23° C. To the vial, imidazolium chloride 2 (14 mg, 26 µmol, 3.0 eq.) and 150 µL of MeCN were added, and the resulting solution mixture was drawn into a 1.0 mL polypropylene syringe.

Target water from the cyclotron containing $^{18}$F-fluoride was loaded with a syringe onto a QMA anion exchange cartridge (Chromafix 30-PS—HCO$_3$) and the radioactivity of the trapped $^{18}$F-fluoride was measured (6.0 mCi, 0.22 GBq). The cartridge was washed with MeCN (1.0 mL). The cartridge was inverted and fitted with a female×female Luer adapter. With the syringe, which contained the corresponding solution of S25-ruthenium complex and 2, the $^{18}$F-fluoride was eluted into a 1 dram (3.7 mL) borosilicate vial. The cartridge was washed with DMSO (150 µL), followed by DMSO: MeCN (50 µL, 1:1 (v/v)) and the radioactivity of the eluted solution was measured (3.0 mCi, 0.11 GBq). The reaction vial, which contained 400 µL of the reaction mixture was sealed with a teflon-lined cap and was heated at 125° C. for 30 min. The vial, which contained the reaction mixture was removed from the heat and was allowed to stand for 3 min at 23° C. The reaction mixture was analyzed by radio-HPLC and radio-TLC. The product 7p was characterized by comparing the radio-HPLC trace of the reaction mixture with the HPLC UV traces of the authentic reference sample.

Kits

The compounds used in the methods described herein (e.g., a hydroxy aryl or heteroaryl compound, the Ru complex and a fluorinating agent) may be provided in a kit. The kit includes (a) a compound used in a method described herein (e.g., a compound of formulas (I) and (II)), the Ru complex and, optionally (b) informational material. The informational material can be descriptive, instructional, marketing or other material that relates to the methods described herein and/or the use of the compounds for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to methods for using the compound.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In some embodiments, the components of the kit are stored under inert conditions (e.g., under Nitrogen or another inert gas such as Argon). In some embodiments, the components of the kit are stored under anhydrous conditions e.g., with a desiccant). In some embodiments, the components are stored in a light blocking container such as an amber vial.

A compound described herein can be provided in any form, e.g., liquid, dried or lyophilized form. It is preferred that a compound described herein be substantially pure and/or sterile. When a compound described herein is provided as a dried form, reconstitution generally is by the addition of a suitable solvent.

The kit can include one or more containers for the composition containing a compound described herein. In some embodiments, the kit contains separate containers, dividers or compartments for the composition and informational material. For example, the composition can be contained in a bottle, vial, or ampule, and the informational material can be contained in a plastic sleeve or packet. In other embodiments, the separate elements of the kit are contained within a single, undivided container. For example, the composition is contained in a bottle, vial or ampule that has attached thereto the informational material in the form of a label. In some embodiments, the kit includes a plurality (e.g., a pack) of individual containers, each containing one or more unit dosage forms (e.g., a dosage form described herein) of a compound described herein. The containers of the kits can be air tight, waterproof (e.g., impermeable to changes in moisture or evaporation), and/or light-tight.

As illustrated above, the new fluorinating process is suitable for site-specific substitution of hydroxyl groups with non-carrier-added 18F-fluoride in a one-step transformation. The transformation combines the substrate scope of late-stage fluorination with the convenient and broadly implemented reaction setup of simple displacement chemistry.

The use of readily available phenols as precursors allows rapid access to new PET probes. Development of this method of radiofluorination into a fully automated, versatile 18F-labeling protocol would considerably streamline tracer development through the synthesis of desirable PET probes.

The invention claimed is:

1. A method of replacing a hydroxyl group on an aryl or heteroaryl compound bearing the hydroxyl group with a fluorine atom, the method comprising contacting a compound of Formula (I):

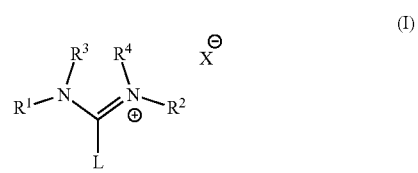

with a Cp-Ru-(aryl or heteroaryl)-complex in the presence of a fluorine source under conditions sufficient to fluorinate the aryl or heteroaryl compound bearing the hydroxyl group compound, thereby providing a fluorinated (aryl or heteroaryl) compound, wherein, in Formula (I):

$R^1$ and $R^2$ are independently selected from the group consisting of C1-30 aliphatic, aromatic, heteroaliphatic or heteroaromatic hydrocarbons, each of which is optionally substituted with at least one substituent selected from C1-20 straight chain, branched or cyclic alkyl, alkenyl, alkynyl, aryl, heteroaryl, each being optionally further substituted by one or more heteroatoms, or heteroatoms, $R^3$ and $R^4$ are independently selected from the group consisting of C1-30 aliphatic, aromatic, heteroaliphatic or heteroaromatic hydrocarbons, each of which is optionally substituted with at least one substituent selected from C1-20 straight chain, branched or cyclic alkyl, alkenyl, alkynyl, aryl, heteroaryl, each being optionally further substituted by one or more heteroatoms, or heteroatoms, or $R^3$ and $R^4$ together with N—C=N to which they are bonded form a C4-20 ring which may be saturated or unsaturated aliphatic or aromatic, which C4-20 ring is optionally substituted with at least one substituent selected from C1-20 straight chain, branched or cyclic alkyl, alkenyl, alkenyl, aryl, heteroaryl, the C4-20 ring being optionally further substituted by one or more heteroatoms, or heteroatoms, and the C4-20 ring optionally fused to a C5-20 hydrocarbon ring which may be unsaturated or saturated aliphatic or aromatic including heteroatoms, which C5-20 hydrocarbon ring is optionally substituted by at least one substituent selected from C1-6 alkyl, C2-6 alkenyl, C2-6 alkynyl, nitro, cyano, halo, C1-6 haloalkyl, C1-6 alkoxy, optionally substituted C6-10 aryl, optionally substituted C6-10 aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, and acyl, each substituent for the C5-20 hydrocarbon ring being optionally further substituted by one or more heteroatoms;

X being an anion; and

L being a leaving group, wherein the Cp-Ru-(aryl or heteroaryl)-complex is a Ru complex with a C5 to C30 aromatic or heteroaromatic mono- to polycyclic ring system having at least one aromatic or heteroaromatic ring with one hydroxyl group on said ring, said ring system optionally being further substituted with straight chain, branched or cyclic alkyl, alkenyl or alkynyl having 1 to 20 carbon atoms, or heteroatoms being selected from halogen, N, O or S, each of said alkyl, alkenyl, alkynyl, or heteroatoms being optionally further substituted or each of said alkyl, alkenyl, alkynyl, or heteroatoms being optionally part of an aliphatic or aromatic ring system, and at least one further ligand optionally being further substituted by one or more heteroatoms or by C1-6 alkyl, optionally being further substituted with halogen.

2. The method according to claim 1, wherein the compound of Formula (I) has the Formula (II):

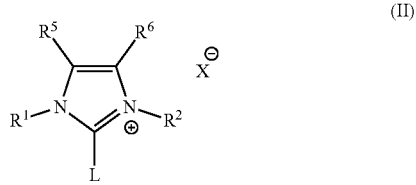

(II)

and the method comprises contacting a compound of Formula (II) with the Cp-Ru-(aryl or heteroaryl)-complex and a fluorine source under conditions sufficient to fluorinate the aryl or heteroaryl compound bearing the hydroxyl group, thereby providing a fluorinated aryl compound, wherein, in Formula (II):

$R^1$ and $R^2$ are independently selected from the group consisting of C1-6 alkyl, C6-10 aryl, C6-10 aralkyl, 5-10 membered heteroaryl, 5-10 membered heteroaralkyl, 4-10 membered heterocyclyl, 4-10 membered heterocyclylalkyl, 3-10 membered carbocyclyl, and 3-10 membered carbocyclylalkyl, each being optionally further substituted by one or more heteroatoms;

$R^5$ and $R^6$ are independently selected from the group consisting of hydrogen, C1-6 alkyl, C2-6 alkenyl, C2-6 alkynyl, nitro, cyano, halo, C1-6 haloalkyl, C1-6 alkoxy, optionally substituted C6-10 aryl, optionally substituted C6-10 aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, each being optionally further substituted by one or more heteroatoms; or $R^5$ and $R^6$ may form together a C5-20 hydrocarbon ring which may be unsaturated or saturated aliphatic or aromatic including heteroatoms, optionally being substituted by C1-6 alkyl, C2-6 alkenyl, C2-6 alkynyl, nitro, cyano, halo, C1-6 haloalkyl, C1-6 alkoxy, optionally substituted C6-10 aryl, optionally substituted C6-10 aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, each being optionally further substituted by one or more heteroatoms;

X being an anion; and

L is a leaving group, wherein the Cp-Ru-(aryl or heteroaryl)-complex is a Ru complex comprising an aryl or heteroaryl compound bearing a hydroxyl group as a ligand and at least one further ligand optionally being substituted by C1-6 alkyl, haloalkyl or halogen.

3. The method according to claim 2, wherein in Formula (II):

$R^1$ and $R^2$ are independently selected from the group consisting of C6-10 aryl, C6-10 aralkyl, 5-10 membered heteroaryl, 5-10 membered heteroaralkyl, each of which is optionally substituted at least one substituent selected from the group consisting of halogen, C1-6 alkyl, C2-6 alkenyl, C2-6 alkynyl, C1-6 haloalkyl, C1-6 alkoxy, optionally substituted with at least one heterosubstituent;

$R^5$ and $R^6$ are independently selected from the group consisting of hydrogen, C1-6 alkyl, C2-6 alkenyl, C2-6 alkynyl, C1-6 haloalkyl, C1-6 alkoxy, optionally substituted C6-10 aryl, optionally substituted C6-10 aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, acyl, optionally substituted with at least one heterosubstituent, L is a leaving group which is not detrimentally interacting in the method; and X represents an anion.

4. The method according to claim 2, wherein the compound of Formula (II) is represented by the following formula (III):

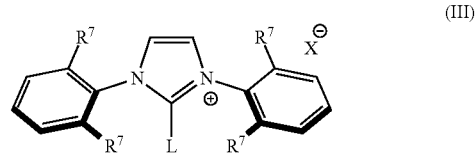

(III)

wherein each $R^7$ is independently selected from halogen, optionally substituted C1-8 alkyl, in particular isopropyl, C1-8 haloalkyl, C1-8 alkoxy, optionally substituted C6-12 aryl, and optionally substituted 6-12 membered heteroaryl, and wherein "substituted" refers to substituted with a substituent selected from the group consisting of alkyl, cycloalkyl, haloalkyl, aryl, heteroaryl, aralkyl, heteroaralkyl, heterocyclyl, alkenyl, alkynyl, cycloalkenyl, heterocycloalkenyl, alkoxy, haloalkoxy, halogen, hydroxy, carboxy, carboxylate, cyano, nitro, amino, alkylamino, dialkylamino, sulfate, phosphate, methylenedioxy —O—$CH_2$—O— wherein oxygens are attached to vicinal atoms, ethylenedioxy, oxo, thioxo (e.g., C=S), imino (alkyl, aryl, aralkyl), $S(O)_n$-alkyl (where n is 0-2), $S(O)_n$-aryl (where n is 0-2), $S(O)_n$-heteroaryl (where n is 0-2), $S(O)_n$-heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof), and wherein L and X are selected from halide ions or carboxylate ions.

5. The method according to claim 1, wherein L and X are selected from halide ions or carboxylate ions.

6. The method according to claim 1 wherein the fluorine source is a fluoride salt.

7. The method according to claim 1, wherein the fluorine source is a sodium, potassium, or cesium fluoride salt.

8. The method according to claim 1, wherein the fluoride source comprises $^{18}$F.

9. The method according to claim 1, wherein the fluoride source comprises $^{19}$F.

10. The method according to claim 1, wherein the Ru phenol complex is a Ru complex with an aryl compound bearing one hydroxyl as a ligand and one cyclopentadienyl ligand, optionally being substituted.

11. A complex of the general formula (IV):

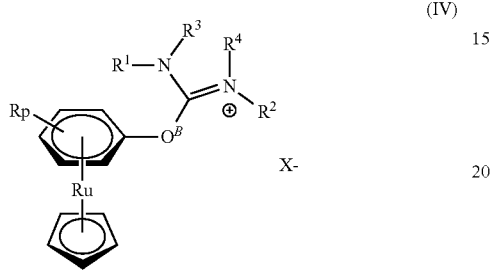

(IV)

wherein in said formula (IV):

represents a C5 to C30 aromatic or heteroaromatic mono- to polycyclic ring system having at least one aromatic or heteroaromatic ring and one oxygen $O^B$ bound on said aromatic or heteroaromatic ring, said ring system optionally being further substituted with at least one substituent $R_p$ selected from straight chain, branched or cyclic alkyl, alkenyl, alkynyl, aryl, heteroaliphatic or heteroaryl each having 1 to 20 carbon atoms, each being optionally further substituted by one or more heteroatoms, or a heteroatom, $R^1$ and $R^2$ are independently selected from the group consisting of C1 to C30 aliphatic, aromatic, heteroaliphatic or heteroaromatic hydrocarbons, each of which is optionally substituted with at least one substituent selected from C1-20 straight chain, branched or cyclic alkyl, alkenyl, alkynyl, aryl, heteroaryl or heteroatoms, each being optionally further substituted by one or more heteroatoms, $R^3$ and $R^4$ are independently selected from the group consisting of C1-30 aliphatic, aromatic, heteroaliphatic or heteroaromatic hydrocarbons, each of which is optionally substituted with at least one substituent selected from C1-20 straight chain, branched or cyclic alkyl, alkenyl, alkynyl, aryl, heteroaryl or heteroatoms, each being optionally further substituted by one or more heteroatoms, or $R^3$ and $R^4$ with N—C=N to which they are bonded form a C4-20 ring which may be saturated or unsaturated aliphatic or aromatic, which C4-20 ring is optionally substituted with at least one substituent selected from C1-20 straight chain, branched or cyclic alkyl, alkenyl, alkynyl, aryl, heteroaryl or heteroatoms, the C4-20 ring being optionally further substituted by one or more heteroatoms, and the C4-20 ring optionally fused to a C5-20 hydrocarbon ring which may be unsaturated or saturated aliphatic or aromatic including heteroatoms, which C5-20 hydrocarbon ring is optionally substituted by at least one substituent selected from C1-6 alkyl, C2-6 alkenyl, C2-6 alkynyl, nitro, cyano, halo, C1-6 haloalkyl, C1-6 alkoxy, optionally substituted C6-10 aryl, optionally substituted C6-10 aralkyl, optionally substituted 5-10 membered heteroaryl, optionally substituted 4-10 membered heterocyclyl, optionally substituted 3-10 membered carbocyclyl, optionally substituted 4-10 membered heterocyclylalkyl, and acyl, each substituent for the C5-20 hydrocarbon ring being optionally further substituted by one or more heteroatoms; and X being an anion.

12. Process for converting a complex of the general formula (IV) as defined in claim 11 into a Cp-Ru-(aromatic or heteroaromatic mono- to polycyclic ring)F complex comprising treating the complex of general formula (IV) with a fluorine source.

13. Process according to claim 12, further comprising decomplexing the Cp-Ru-(aromatic or heteroaromatic mono- to polycyclic ring)F complex whereby a fluorinated aromatic or heteroaromatic mono- to polycyclic ring is obtained.

* * * * *